United States Patent [19]

Melzer et al.

[11] 4,217,108
[45] Aug. 12, 1980

[54] PROCESS FOR THE QUANTITATIVE DETERMINATION OF THE CARBON OF ORGANIC COMPOUNDS IN WATER

[75] Inventors: Werner Melzer, Liederbach; Dieter Jaenicke; Helmut Schroeder, both of Hofheim am Taunus, all of Fed. Rep. of Germany

[73] Assignee: Hoechst Aktiengesellschaft, Frankfurt, Fed. Rep. of Germany

[21] Appl. No.: 20,039

[22] Filed: Mar. 13, 1979

[30] Foreign Application Priority Data

Mar. 15, 1978 [DE] Fed. Rep. of Germany ....... 2811135

[51] Int. Cl.² ...................... G01N 31/12; G01N 33/18
[52] U.S. Cl. .................................. 23/230 PC; 23/906; 422/79
[58] Field of Search ............... 23/230 PC, 906; 422/79

[56] References Cited

U.S. PATENT DOCUMENTS

| | | | |
|---|---|---|---|
| 3,296,435 | 1/1967 | Teal et al. | 422/79 X |
| 3,459,938 | 8/1969 | Stenger et al. | 422/79 X |
| 3,607,071 | 9/1971 | Staffin et al. | 422/79 X |
| 3,840,341 | 10/1974 | Rogers | 23/230 PC |
| 3,930,798 | 1/1976 | Schierjott et al. | 422/79 X |
| 3,955,924 | 5/1976 | Northmore et al. | 422/79 X |

Primary Examiner—R. E. Serwin
Attorney, Agent, or Firm—Curtis, Morris & Safford

[57] ABSTRACT

In the determination of the quantity of carbon present in water in the form of organic compounds the carbon-containing water is first evaporated in the presence of oxygen at a temperature of about 900° C. Care must be taken that the oxygen does not exceed 1 to 5 volume %, calculated on the quantity of steam. Then the $CO_2$ content is measured with a $CO_2$ analyzer. In a second step the carbon-containing water is measured without oxygen under identical conditions. The quantity of carbon present in water in the form of organic compounds is determined from the measured $CO_2$ concentrations.

4 Claims, 1 Drawing Figure

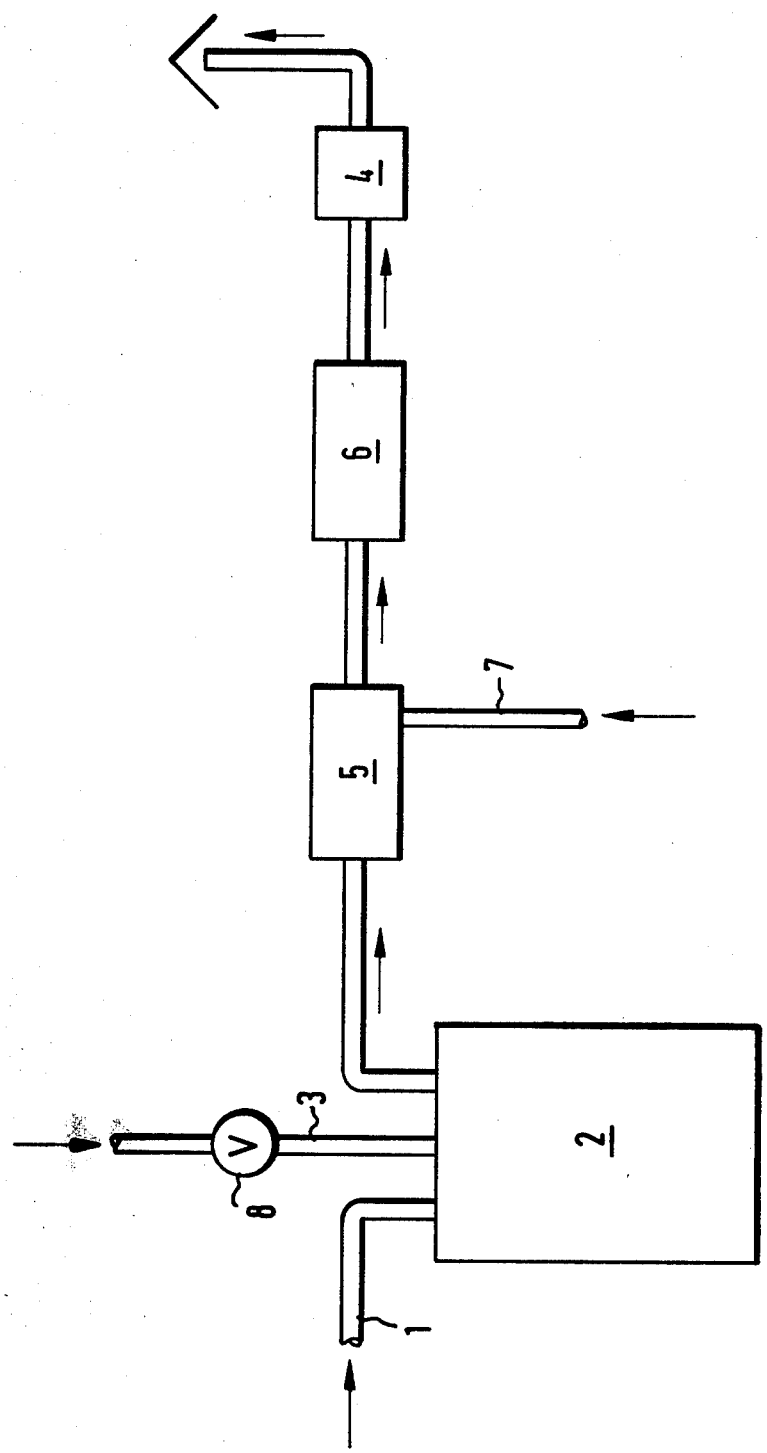

PROCESS FOR THE QUANTITATIVE DETERMINATION OF THE CARBON OF ORGANIC COMPOUNDS IN WATER

The present invention relates to a process for the quantitative determination of the total carbon present in water in the form of organic compounds.

The abbreviations used in the present invention are defined as follows:

TC (Total Carbon) means the total carbon present in water;

TAC (Total Anorganic Carbon) means the total carbon present in water in the form of inorganic compounds;

TOC (Total Organic Carbon) means the total carbon present in water in the form of organic compounds;

oxygen means pure oxygen and all oxygen-containing gases, in particular air.

TOC determinations are known. In these methods the TC and the TAC are measured and the TOC is calculated from the difference between both contents. For analyzing the water, a small amount thereof is fed into a reactor heated to about 900° C., through which a large flow of a constant volume of oxygen-containing carrier gas passes. The volume ratio between steam and carrier gas is about 1:100. In the reactor the carbon, if any, is converted into $CO_2$, which is subsequently in an infrared photometer. For determining the TAC, water and carrier gas are introduced at the same volume ratio as above into a phosphoric acid recipient maintained at 150° C. In this process the carbon present in the form of inorganic compounds is converted into $CO_2$ which is likewise measured with the infrared photometer. The difference between TC and TAC corresponds to TOC. This method has the disadvantage that the water sample dosage must be measured with great accuracy, particularly in the case of highly polluted water.

It was, consequently, an object of the present invention to develop a process, in which the dosage accuracy requirements are minimized.

Thus the present invention provides a process for the quantitive determination of the carbon of organic compounds in water (a) by evaporating the carbon-containing water in the presence of oxygen at a temperature of about 900° C., the quantity of oxygen being necessarily not more than 1 to 5 volume %, calculated on the quantity of steam, and measuring the $CO_2$ concentration, (b) by evaporating the carbon-containing water without oxygen at a temperature of about 900° C. and measuring the $CO_2$ concentration, (c) by determining the TOC from $CO_2$ concentrations measured in steps (a) and (b).

If care is taken that the temperature does not drop below the dew point, the $CO_2$-containing steam may be introduced directly into the $CO_2$ analyzer. Alternatively, the $CO_2$-containing steam may be added to a constant flow of $CO_2$-free carrier gas, from which the steam is removed subsequently, for example by condensation, prior to determining the $CO_2$ concentration. In this method the volume ratio between steam and carrier gas should be kept as constant as possible.

The process according to the invention makes it possible to control in a particularly advantageous manner the hydrocarbon content of waste waters. Another point worth mentioning is the fact that the process in nearly insensitive to variations in the dosage rate of the water samples. For example, with a volume ratio between air and steam of 1:100 and a variation of the water dosage by a factor of 2, the error limit is 2% only, calculated on the measured value. A further advantage resides in the fact that the reaction of the carbon present in the form of inorganic compounds proceeds under completely identical conditions, both in the TC determination and in the TAC determination so that the TOC value cannot be falsified. However, when $CO_2$ is separated from organic compounds in the water in the reaction vessel without the addition of oxygen the TAC value increases, as a consequence of which the TOC value is falsified.

The invention will be illustrated, by way of example only, in the accompanying figure representing a flow scheme of the process of the invention.

Referring now the the FIGURE: In a reaction vessel 2 fed continuously with water through conduit 1 and with air through conduit 3, water is evaporated at about 900° C. and the carbon present in the water is converted to $CO_2$. The quantity of oxygen should be sufficiently high for bringing about the carbon conversion. Quantities of oxygen from 1 to 5 volume %, calculated on the volume of the steam, have proved sufficient. The $CO_2$-containing steam leaving the reaction vessel 2 is conveyed to a $CO_2$ analyzer 4, for example an infrared photometer, where the $CO_2$ concentration is measured. Care should be taken that the temperature does not drop below the dew point of the water on the way to the $CO_2$ analyzer 4 as well as during the $CO_2$ measurement. In a further embodiment of the process of the invention the $CO_2$-containing steam is added through a dosing device 5 to a constant flow of $CO_2$-free carrier gas 7, for example in a volume ratio of 1:4. In device 6 the steam is removed from the mixture of carrier gas and $CO_2$-containing steam, for example by drying or condensing, then the $CO_2$ cannot of the gas is determined. In this embodiment a condensation of steam on its way to device 6 must be avoided. For measuring the TAC, the admission of the oxygen-containing gas through valve 8 is interrupted.

EXAMPLE

Water which is polluted by 0.750 g of butanol as organic matter and by 5 g/l of sodium bicarbonate as inorganic matter, is conveyed continuously by a pump at a rate of 30 g/h into a reaction furance having a capacity of about 90 ml.

The $CO_2$-containing steam of the reactor is added to a constant flow of $CO_2$-free carrier gas in a ratio of 1:4 and the water is removed by condensation prior to determining the $CO_2$ content by the infrared photometer. A $CO_2$ concentration of 300 ppm by volume is measured in the case of oxygen addition to the reaction furance of 1.2 liter/hour. After interruption of the $O_2$ addition to $CO_2$ content of 120 ppm by volume is measured.

The difference between TC and TAC gives a TOC of 180 ppm by volume, which corresponds to a carbon content in the form of organic compounds of 0.487 g/l.

What is claimed is:

1. A process for the quantitative determination of total organic carbon present in water (TOC), which comprises
    (a) determining the total carbon present in water (TC) by evaporating carbon-containing water at a temperature of about 900° C. in the presence of oxygen to form a $CO_2$-containing steam wherein said oxygen is present in an amount of from 1 to 5 volume percent calculated on the amount of steam and then measuring the $CO_2$ concentration, (b) determining the total inorganic carbon present in water (TAC) by evaporating carbon-containing water at a temperature of about 900° C. without oxygen and then measuring the $CO_2$ concentration, and (c) determining the TOC by taking the difference between the TC and TAC values.

2. The process as claimed in claim 1, which comprises adding the $CO_2$-containing steam to a constant flow of carrier gas free from $CO_2$, removing the steam and determining the $CO_2$ concentration.

3. The process as claimed in claim 1, which comprises determining the $CO_2$ concentration at a temperature of at least 100° C.

4. The process as claimed in claim 2, which comprises adding the $CO_2$-containing steam to the carrier gas in a volume ratio of 1:4.

* * * * *